United States Patent [19]

Cabe, Jr. et al.

[11] Patent Number: 4,859,519
[45] Date of Patent: Aug. 22, 1989

[54] METHOD AND APPARATUS FOR PREPARING TEXTURED APERTURED FILM

[76] Inventors: Alex W. Cabe, Jr., 3 Muierfield Ln., Lebanon, N.J. 08833; Robert W. Saffel, 124 Dey St., Hightstown, N.J. 08520; Arthur J. Sampson, R.D. 1 Blackwell Mills Rd., Belle Meade, N.J. 08502

[21] Appl. No.: 92,862

[22] Filed: Sep. 3, 1987

[51] Int. Cl.⁴ .................... B32B 3/10; B29C 59/04
[52] U.S. Cl. ................................ 428/131; 264/156; 264/284; 425/290; 425/304; 428/141; 428/156
[58] Field of Search ............ 264/284, 147, 154, 156; 428/913, 131, 141, 156; 425/290, 304

[56] References Cited

U.S. PATENT DOCUMENTS

| | | | |
|---|---|---|---|
| 3,632,269 | 1/1972 | Doviak et al. | 264/154 X |
| 3,810,729 | 5/1974 | Patchell | 264/147 X |
| 4,259,286 | 3/1981 | Louis et al. | 264/284 X |
| 4,272,473 | 6/1981 | Riemersma et al. | 264/154 |
| 4,329,309 | 5/1982 | Kelly | 264/154 X |
| 4,463,045 | 7/1984 | Ahr et al. | 428/913 X |
| 4,690,679 | 9/1987 | Mattingly, III et al. | 604/383 |

Primary Examiner—Philip Anderson

[57] ABSTRACT

Apertured polymeric films for use as a liquid permeable facing material on absorbent products such as diapers and sanitary napkins is textured by a dual embossing process. The film is preferably embossed first with a pronounced, textile-like pattern, then embossed with a finely engraved finish roll to produce a thin, smooth film with a matte finish while retaining the appearance of the previously embossed pattern. The twice embossed film is soft, conformable, and more comfortable against the skin. The embossing sequence may be reversed for some applications.

34 Claims, 3 Drawing Sheets

METHOD AND APPARATUS FOR PREPARING TEXTURED APERTURED FILM

FIELD OF THE INVENTION

This invention relates to apertured plastic films for use in absorbent products and, more specifically, to a method and apparatus for imparting a desirable appearance and texture to such film.

BACKGROUND

Absorbent products such as diapers, sanitary napkins and the like generally include a liquid permeable cover on one surface which may be fabric or apertured film. The purpose of the cover is to structurally contain the loosely packed absorbent material which comprises the bulk of the absorbent product, and to protect the body from direct contact with the absorbent material. The cover is preferably nonabsorbent so that the surface of the cover maintains a dry feel while fluids pass through the cover into the absorbent core. Since the cover material is in direct contact with the body, it should be smooth, soft and comfortable to the touch. Certain visual characteristics such as color, lustre, and texture are also important to consumer acceptance and satisfaction.

Apertured films of polypropylene and polyethylene have been widely used as cover materials for absorbent products since these films are inexpensive, nonabsorbent and readily produced. A particularly preferred material for use as a cover is a coextruded film of polyethylene and ethylene vinyl acetate (EVA) as described in U.S. Pat. No. 4,690,679. The polyethylene side of the film which is used as the body contact side, has a higher melting point than the EVA side of the film which permits the film to be thermally bonded while maintaining structural integrity. The outer polyethylene component of the film may be delustred with calcium carbonate while the EVA component may be pigmented with $TiO_2$ to increase the opacity of the film.

The polyethylene, coextruded polyethylene/EVA or other polymeric film is impervious to liquids as produced, and must be perforated or otherwise apertured for use as a liquid permeable cover material. The film may be perforated by known methods such as needle punching, pin perforating, embossing and stretching, or roll forming as disclosed in U.S. Pat. No. 4,690,679. Alternatively, the film may be extruded with a solid particulate component which is subsequently removed from the film by stretching and/or mechanical or chemical means. These and other methods may be utilized to produce an apertured, liquid permeable film for use as a cover material on absorbent products.

Apertured films as produced by the aforementioned methods have the desired liquid permeability and other functional properties, but are often lacking in aesthetics. In particular, these films may retain the "plastic" feel characteristic of polymeric films, and may be sticky or uncomfortable in contact with the skin of the user. Moreover, some methods of perforation may impart a certain degree of roughness to the surface of the film which further decreases comfort and consumer acceptance. In this regard, certain nonabsorbent but liquid permeable woven and nonwoven fabrics have superior softness and comfort as compared to apertured films.

It is accordingly an object of the present invention to provide a film having improved softness and hand with certain textile like properties. It is a further object of this invention to provide an apertured film having improved comfort and consumer acceptance when used as the liquid permeable cover on absorbent products. It is a yet further object of this invention to provide a method and apparatus for modifying apertured film in order to enhance the texture and physical properties thereof. These and other objects of this invention will be apparent from the ensuing description and claims.

SUMMARY

In accordance with the preferred method of the present invention, apertured film for use as a cover material for absorbent products is subjected to a dual embossing process wherein the film is first macro embossed to expand the film out of the plane of the film in the thickness or Z-direction and impart a pronounced pattern to the surface of the film, and thereafter micro embossed with a finely engraved finish roll to flatten the structure into a thin, smooth film and impart a matte finish to the film while retaining the textile imprint of the macro embossing. The resulting product is a substantially two dimensional film having a smooth textured surface, low gloss and improved hand and softness.

In an alternate embodiment, the order of embossing may be reversed wherein the apertured film is first embossed with the micro embossing roll followed by macro embossing. The resulting product retains the micro embossed matte finish, but is highly expanded in the Z-direction following the macro embossing. The film accordingly has considerably greater loft or bulk than the macro-micro embossed film and may be preferred for certain end use applications.

The doubly embossed film retains its structural integrity and can be processed and assembled on absorbent products using conventional methods and equipment. The embossing reduces average hole size but increases hole size distribution which may be advantageous for certain applications. The processed film has improved hand, appears softer and less "plastic" by subjective tests and is more comfortable in contact with the body.

DESCRIPTION OF THE INVENTION

Figure 1:
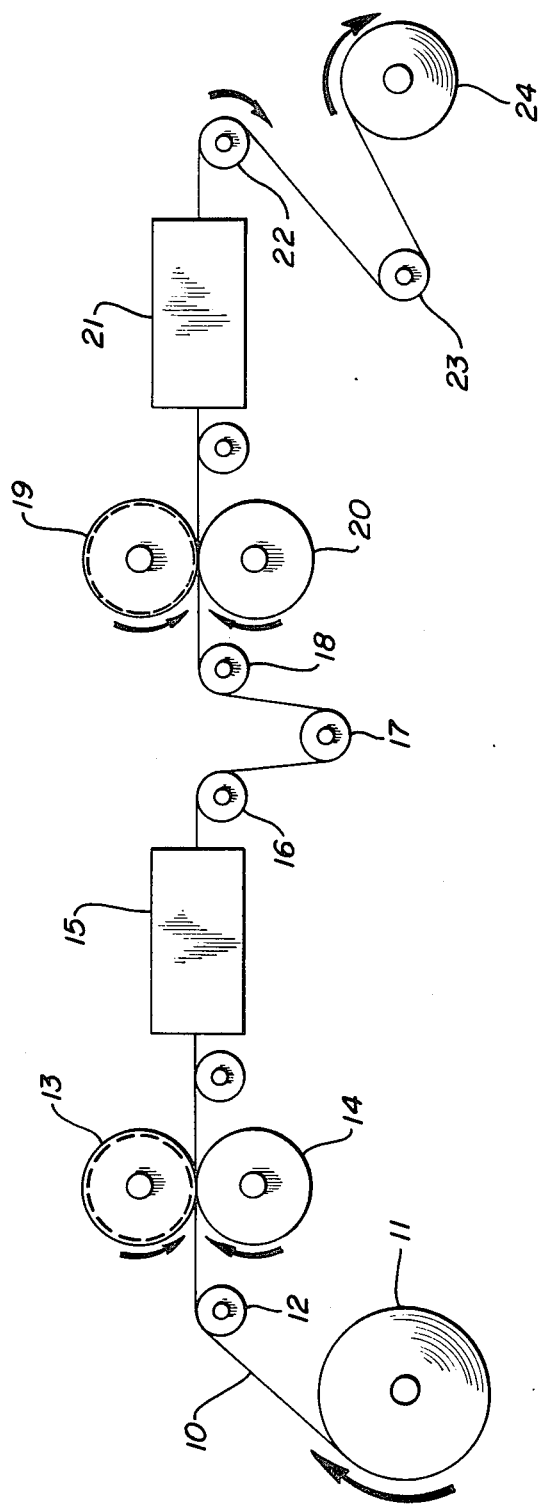
FIG. 1 schematically illustrates the dual embossing process of the present invention.
Figure 2:
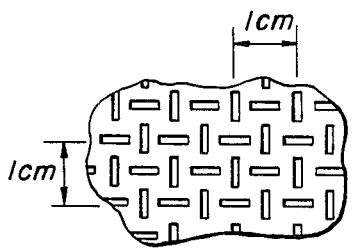
FIGS. 2, 3 and 4 are enlarged plan views of various embossing patterns which may be utilized on a macro roll.
Figure 3:
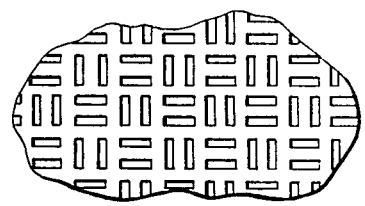
Figure 4:
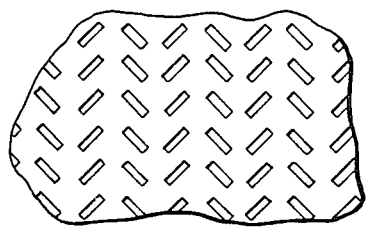

In accordance with a preferred method of the present invention, a supply of apertured film, preferably in the form of rolled goods, is processed through a dual embossing station, substantially as illustrated in FIG. 1. Apertured film 10, such as that obtained by the process of U.S. Pat. No. 4,690,679, is fed from roll 11, over idler roll 12, to the first embossing station comprising macro embossing roll 13 and rubber coated anvil roll 14. Embossing roll 13 is a steel roll having a pronounced embossing pattern such as the textile-like patterns illustrated in FIGS. 2-4, where FIG. 2 illustrates a cross-dash pattern, FIG. 3 illustrates a basket-weave pattern, and FIG. 4 illustrates a herringbone pattern. Anvil roll 14 is a steel roll having a rubber sleeve to provide a resilient backing surface for the embossing roll. Rolls 13 and 14 are individually driven at synchronized speeds to draw film 10 off roll 11. Embossing roll 13 is heated and forced against anvil roll 14 under controlled pressure, the optimum temperature and pressure being dependent upon the thickness and composition of the film and the embossing speed. Specific operating conditions are best determined experimentally for each particular film. If embossing conditions are too mild, i.e. temperature and/or pressure too low, the film will be insufficiently embossed and the desired deformation and pattern definition will not be obtained. If conditions are too severe, i.e. temperature and/or pressure too high, there will be excessive plastic flow resulting in extreme thinness and possibly holes in the land areas of the embossed film. In general, an embossing temperature greater than about 150° F. will be used for polyolefin films.

While the macro embossing rolls preferably have a textile-like pattern, it will be understood that any macro embossing pattern comprising a multiplicity of projections in a regular or random pattern may be utilized according to the desired appearance of the final product. Each projection preferably has a face comprising a planer area, referred to herein as a "land", and the projections may comprise two or more contiguous lands forming, for example, a chevron, right-angle or grid-type configuration. Since the film is stretched in the Z-direction during the embossing process, sufficient free area between lands must be provided to avoid overstressing and rupturing the film. While the minimum required free area will depend to some extent on the thickness and composition of the film, as well as on the height of the projections, in most cases the free area should comprise from 0.5 to 10 times the land area, and most preferably from 1 to 7 times the land area. Greater proportions of free area can be provided of course, but the embossing is less effective if the land area is substantially less than 10 percent of the total surface area of the roll.

Apertured polymeric film for use as a cover material for absorbent products generally has a thickness of from about 1 to 30 mils, and most preferably from about 3 to 10 mils. The projections on the macro embossing roll preferably have a height of at least 0.3 mm, and most preferably from 0.5 to 1.0 mm. The projections are preferably tapered inwardly from the base to the land in order to reduce stress on the film during the embossing process. In this regard, the macro embossing rolls of the present invention conform to conventional practice for rolls intended to emboss plastic film.

Film leaving the macro embossing station is preferably passed through a chiller and around tensioning rolls before moving on to the micro embossing station. The chiller, illustrated schematically as 15 in FIG. 1, may consist of cooled rolls or a cool air stream and preferably reduces the film temperature to less than about 100° F. before the film contacts idler roll 16. The cooled film passes around tensioning roll 17 and idler roll 18 before feeding into the micro embossing station comprising embossing roll 19 and anvil roll 20. Rolls 19 and 20 are independently driven by synchronous means which respond to the position of tensioning roll 17 in order to assure constant tension with uniform feed between the two embossing stations. The micro embossing roll 19 is a steel roll engraved with a fine pattern such as that illustrated in FIGS. 5–7. Anvil roll 20 is a steel roll with a nylon sleeve which forms a firm backing surface for the micro embossing roll. Embossing roll 19 is heated and forced against the anvil roll at a temperature and pressure determined by the thickness and composition of the film, the nature of the pattern imparted by the macro embossing station, and the speed of the operation. Optimum processing conditions are best determined experimentally for each operation.

Figure 5:
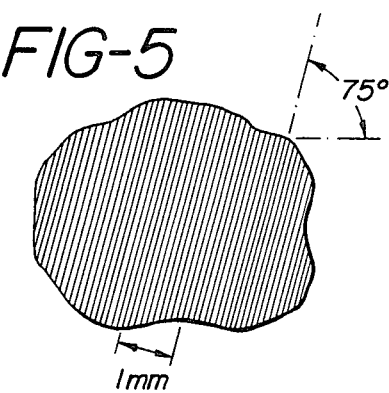
FIGS. 5, 6 and 7 are enlarged plan views of various embossing patterns which may be utilized on the micro embossing roll.
Figure 6:
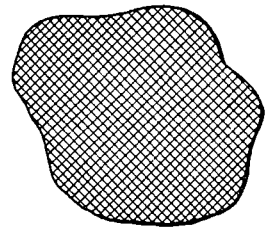
Figure 7:
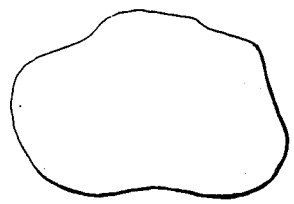

The micro embossing rolls are provided with a finely engraved or otherwise suitably prepared surface to impart a matte finish to the film. As illustrated in FIG. 5, one suitable embossing pattern comprises a series of parallel lines angled to the major axis of the roll with from about 2 to 20 lines per millimeter and each line cut to a depth of about 0.03 mm, this pattern being known in the art as a Schreiner pattern. FIG. 6 illustrates a cross-cut pattern of intersecting lines at a 45° angle, and similar patterns of intersecting lines forming angles of 15° to 75° with the major axis of the roll may be used. FIG. 7 illustrates a granular surface which may have regular or random projections and indentations formed by mechanical, chemical or electrochemical processing. In all these rolls, the desired effect is obtained if the surface texture of the roll is sufficient to impart a matte finish to the film during the micro embossing process.

Upon leaving the micro embossing station, the film passes through chiller 21, over idler roll 22, around tensioning roll 23, and onto windup 24. Chiller 21 preferably comprises refrigerated steel rolls to cool the film to about room temperature before the film is collected on windup 24.

The process of the present invention is further illustrated by the following example wherein the starting material was a coextruded apertured film comprising polyethylene and ethylene vinyl acetate as disclosed in U.S. Pat. No. 4,690,679. The film had an average open area of about 42%, a thickness of about 4.5 mils, and a weight of about 1 oz. per sq. yard. The apertures had an average equivalent hydraulic diameter of about 0.016 inches and an average center-to-center spacing of about 0.028 inches.

The apertured film was fed to the macro embossing station with the polyethylene side facing the steel embossing roll and the EVA side against the anvil roll. The speed of the macro embossing rolls was set at about 60 yds. per minute (ypm) and roll nip pressure was about 225 lbs. per linear inch (pli). The embossing roll had a cross-dash pattern corresponding to that illustrated in FIG. 2 with a projection height of 0.7 mm. The ratio of free area to land area was about 4:1. The roll was heated to a temperature of about 170° F. The anvil roll was covered with ½ inch smooth rubber having a hardness value of about 60° on the Shore A scale. During operation, the anvil roll was not cooled and the surface temperature of this roll increased to about 115° F.

After macro embossing, the film was cooled to room temperature and rewound. The film was subsequently processed through the micro embossing station at a speed of 95 ypm under a nip pressure of 500 pli. The micro embossing roll was engraved with the linear pattern illustrated in FIG. 5 cut to a depth of 0.03 millimeters, and was heated to 170° F. The anvil roll was covered with a smooth, 1 inch nylon sleeve having a hardness of about 100° on the Shore A scale. During operation, the anvil roll was not cooled and reached a surface temperature of about 97° F. The resulting film was subsequently cooled to room temperature and collected on a rewind roll.

Figure 8:
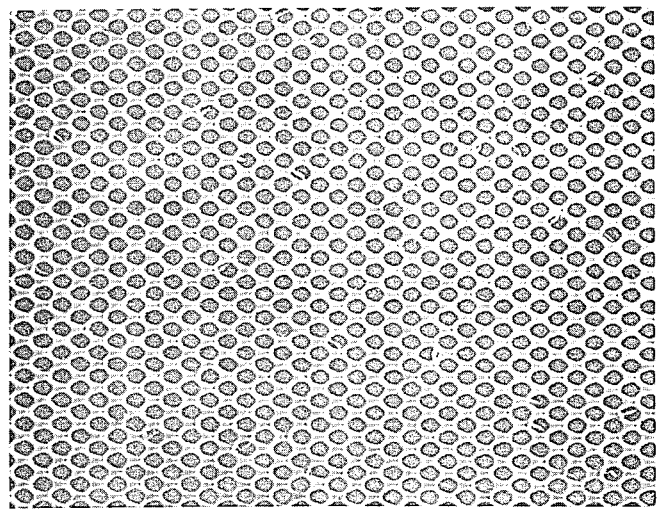
FIG. 8 is an enlarged photograph of the surface of a preferred apertured film before embossing.
Figure 9:
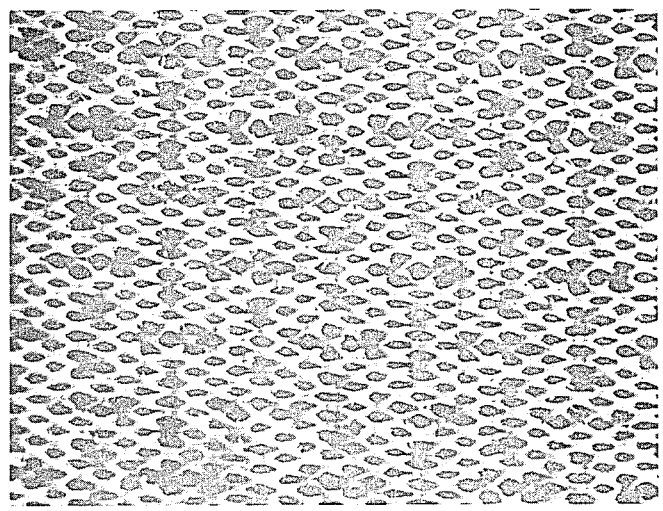
FIG. 9 is an enlarged photograph of the surface of the same apertured film after embossing.

The apertured film which formed the starting material in the above example is illustrated in FIG. 8 which is a photograph of the film surface enlarged 5×. The product resulting from the above example is illustrated in FIG. 9 which is also a surface photograph illustrated 5×. The change in film texture which is readily visible in the photographs translates into a significant improvement in hand, appearance, softness, comfort against the skin, and consumer acceptance when used as a cover material for absorbent products.

The preceding description and examples are directed to a preferred embodiment of the present invention, and many variations therein are possible and within the scope of the invention. For example, a variety of embossing patterns may be utilized on the macro embossing roll other than those illustrated in FIGS. 2–4. Any embossing roll which imparts a pronounced pattern to the film without rupturing the film can be used with good results, the important consideration being that the macro embossing process should expand the film at least about 2× in the Z-direction and impart a distinct and visually pleasing pattern.

The micro embossing roll may likewise comprise patterns other than those illustrated in FIG. 5–7, the important consideration being that the micro embossing roll has a pattern which imparts a low sheen matte finish to the plastic film, thereby enhancing its smoothness and visual appearance. In a less preferred embodiment, micro embossing roll 19 may be a smooth roll, although this results in a higher gloss and diminished textile-like appearance in the finished product.

These and other variations will be apparent to those skilled in the art, and the present invention is accordingly not limited except by the claims appended hereto.

We claim:

1. A process for imparting surface texture and smoothness to an apertured polymeric film comprising:
   a. macro embossing an apertured film having a unit thickness in the Z-direction at an elevated temperature and pressure to expand the film in the Z-direction and impart a pronounced pattern to said film, and
   b. micro embossing said macro embossed film to reduce the thickness of the film in the Z-direction to substantially its original unit thickness while retaining the macro embossed pattern therein.

2. The process of claim 1 wherein said film is expanded in the Z-direction to at least twice its original unit thickness by said macro embossing.

3. A process of claim 1 wherein said apertured film is selected from the group consisting of polypropylene, polyethylene and bicomponent polyethylene/ethylene vinyl acetate.

4. A process of claim 1 wherein said apertured film has an original unit thickness of from 1 to about 30 mils.

5. A process of claim 1 wherein said apertured film has an original unit thickness of from about 3 to 10 mils.

6. A process of claim 1 wherein said film comprises polyethylene and said macro embossing temperature is greater than about 150° F.

7. A process of claim 6 wherein said film is cooled to less than about 100° F. after macro embossing and before micro embossing.

8. A process of claim 6 wherein said film is coextruded polyethylene/ethylene vinyl acetate having a thickness of about 4.5 mils and an average open area of about 40%.

9. The process of claim 1 wherein said pronounced pattern is a textile-like pattern selected from the group consisting of cross-dash, herringbone and basket weave patterns.

10. The process of claim 1 wherein said micro embossing roll comprises an engraved linear pattern.

11. A process for imparting surface texture and softness to an apertured polymeric film comprising
    a. micro embossing said film at an elevated temperature and pressure with a roll having a surface texture sufficient to impart a low reflectance matte finish surface to said film, and
    b. macro embossing said micro embossed film to expand the film in the Z-direction and impart a pronounced pattern to said film while retaining the micro embossed matte finish thereon 12. The process of claim 11 wherein said film is expanded in the Z-direction to at least twice its original thickness by said macro embossing.

13. A process of claim 11 wherein said apertured film is selected from the group consisting of polypropylene, polyethylene and bicomponent polyethylene/ethylene vinyl acetate.

14. A process of claim 11 wherein said apertured film has an original thickness of from 1 to about 30 mils.

15. A process of claim 11 wherein said apertured film has an original thickness of from about 3 to 10 mils.

16. A process of claim 11 wherein said film comprises polyethylene and said micro and macro embossing temperatures are greater than about 150° F.

17. A process of claim 16 wherein said film is cooled to less than about 100° F. after micro embossing and before macro embossing.

18. A process of claim 11 wherein said film is coextruded polyethylene/ethylene vinyl acetate having a thickness of about 4.5 mils and an average open area of about 40%.

19. The process of claim 11 wherein said pronounced pattern is a textile-like pattern selected from the group consisting of cross-dash, herringbone and basket weave patterns.

20. The process of claim 11 wherein said micro embossing roll comprises an engraved linear pattern.

21. An apertured polymeric film produced by the process of claim 1.

22. An apertured polymeric film produced by the process of claim 11.

23. Apparatus for imparting surface texture and smoothness to apertured polymeric films comprising:
    a. macro embossing means comprising a steel embossing roll and a resilient anvil roll, the surface of said macro embossing roll being provided with a prominent pattern of raised projections;
    b. micro embossing means comprising a steel embossing roll and a nonresilient anvil roll, the surface of said micro embossing roll being provided with a surface texture sufficient to impart a matte finish to said polymeric film, and
    c. means for passing said apertured polymeric film through said micro and macro embossing means and for thereafter collecting said film.

24. The apparatus of claim 23 wherein said projections on said macro embossing roll have a height of from about 0.3 to 1.0 millimeters.

25. The apparatus of claim 24 wherein said projections on said macro embossing roll are in a textile-like cross-dash, basket weave or herringbone pattern.

26. The apparatus of claim 26 wherein said resilient anvil roll has a rubber surface and a Shore A hardness of about 60 degrees.

27. The apparatus of claim 23 wherein said nonresilient anvil has a nylon surface with a Shore A hardness of about 100 degrees.

28. The apparatus of claim 23 wherein the surface of said micro embossing roll is engraved in a linear pattern.

29. The apparatus of claim 28 wherein said linear pattern comprises a series of closely spaced parallel lines at an angle of from about 15° to 75° to the major axis of the roll.

30. The apparatus of claim 29 wherein said parallel lines are spaced apart about 0.1 millimeter and have a depth of about 0.03 millimeter.

31. The apparatus of claim 29 wherein said linear pattern comprises a first series of closely spaced parallel lines intersected at an angle by a second series of closely spaced parallel lines.

32. The apparatus of claim 23 further comprising means for cooling said film after said micro embossing and before said wind-up.

33. The apparatus of claim 23 further comprising means for cooling said film intermediate said macro and said micro embossing means.

34. The apparatus of claim 23 wherein the free area between said projections on said macro embossing roll is from 0.5 to about 10 times the land surface area of said projections.

* * * * *

UNITED STATES PATENT AND TRADEMARK OFFICE
CERTIFICATE OF CORRECTION

PATENT NO. : 4,859,519

DATED : August 22, 1989

INVENTOR(S) : Cabe, Jr. et al.

It is certified that error appears in the above-identified patent and that said Letters Patent is hereby corrected as shown below:

In Column 7, Claim 26, line 5, "26" should be -- 23 --.

Signed and Sealed this

Nineteenth Day of October, 1993

Attest:

BRUCE LEHMAN

Attesting Officer

Commissioner of Patents and Trademarks